(12) United States Patent
McFerran et al.

(10) Patent No.: US 7,896,861 B2
(45) Date of Patent: *Mar. 1, 2011

(54) CATHETER WITH A PRE-SHAPED DISTAL TIP

(75) Inventors: Sean McFerran, Newark, CA (US);
Roger Farnholtz, Fremont, CA (US);
Gitanjali V. Barry, Fremont, CA (US);
Kirsten C. Armstrong, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/577,841

(22) Filed: Oct. 13, 2009

(65) Prior Publication Data

US 2010/0030191 A1 Feb. 4, 2010

Related U.S. Application Data

(63) Continuation of application No. 10/970,204, filed on Oct. 21, 2004, now Pat. No. 7,621,904.

(51) Int. Cl.
*A61M 25/00* (2006.01)
(52) U.S. Cl. ..................... 604/525; 604/526
(58) Field of Classification Search .......... 604/523–532
See application file for complete search history.

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,683,904 A | 8/1972 | Forster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,447,227 A | 5/1984 | Kotsanis | |
| 4,568,338 A | 2/1986 | Todd | |

(Continued)

FOREIGN PATENT DOCUMENTS

DE 2821048 A1 7/1980

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner*—Theodore J Stigell
(74) *Attorney, Agent, or Firm*—Seager, Tufte & Wickhem, LLC

(57) ABSTRACT

Catheters having a pre-shaped tip configuration are disclosed. A catheter in accordance with an illustrative embodiment of the present invention can include an elongated tubular shaft equipped with a distal tip section having a pre-shaped tip configuration that can be used to facilitate tracking of the device through particular locations of the vasculature. The catheter may include a number of features that transition the stiffness and flexibility characteristics of the device and provide a means to radiographically visualize the catheter within the body.

16 Claims, 4 Drawing Sheets

U.S. PATENT DOCUMENTS

| | | | |
|---|---|---|---|
| 4,580,568 A | 4/1986 | Gianturco | |
| 4,590,938 A | 5/1986 | Segura et al. | |
| 4,613,324 A | 9/1986 | Ghanjar | |
| 4,619,246 A | 10/1986 | Molgaard-Nielsen et al. | |
| 4,631,052 A | 12/1986 | Kensey | |
| 4,643,184 A | 2/1987 | Mobin-Uddin | |
| 4,650,466 A | 3/1987 | Luther | |
| 4,662,885 A | 5/1987 | DiPisa, Jr. | |
| 4,671,291 A * | 6/1987 | Wilson | 600/435 |
| 4,705,517 A | 11/1987 | DiPisa, Jr. | |
| 4,706,671 A | 11/1987 | Weinrib | |
| 4,723,549 A | 2/1988 | Wholey et al. | |
| 4,728,319 A | 3/1988 | Masch | |
| 4,733,665 A | 3/1988 | Palmaz | |
| 4,790,812 A | 12/1988 | Hawkins, Jr. et al. | |
| 4,790,813 A | 12/1988 | Kensey | |
| 4,794,928 A | 1/1989 | Kletschka | |
| 4,794,931 A | 1/1989 | Yock | |
| 4,800,882 A | 1/1989 | Gianturco | |
| 4,807,626 A | 2/1989 | McGirr | |
| 4,842,579 A | 6/1989 | Shiber | |
| 4,857,045 A | 8/1989 | Rydell | |
| 4,857,046 A | 8/1989 | Stevens et al. | |
| 4,867,157 A | 9/1989 | McGurk-Burleson et al. | |
| 4,873,978 A | 10/1989 | Ginsburg | |
| 4,882,777 A | 11/1989 | Narula | |
| 4,886,061 A | 12/1989 | Fischell et al. | |
| 4,898,575 A | 2/1990 | Fischell et al. | |
| 4,898,591 A * | 2/1990 | Jang et al. | 604/527 |
| 4,907,336 A | 3/1990 | Gianturco | |
| 4,921,478 A | 5/1990 | Solano et al. | |
| 4,921,484 A | 5/1990 | Hillstead | |
| 4,926,858 A | 5/1990 | Giffort, III et al. | |
| 4,950,277 A | 8/1990 | Farr | |
| 4,955,895 A | 9/1990 | Sugiyama et al. | |
| 4,957,482 A | 9/1990 | Shiber | |
| 4,969,891 A | 11/1990 | Gewertz | |
| 4,979,951 A | 12/1990 | Simpson | |
| 4,986,807 A | 1/1991 | Farr | |
| 4,998,539 A | 3/1991 | Delsanti | |
| 5,002,560 A | 3/1991 | Machold et al. | |
| RE33,569 E | 4/1991 | Gifford, III et al. | |
| 5,007,896 A | 4/1991 | Shiber | |
| 5,007,917 A | 4/1991 | Evans | |
| 5,011,488 A | 4/1991 | Ginsburg | |
| 5,019,088 A | 5/1991 | Farr | |
| 5,041,126 A | 8/1991 | Gianturco | |
| 5,053,008 A | 10/1991 | Bajaj | |
| 5,053,044 A | 10/1991 | Mueller et al. | |
| 5,071,407 A | 12/1991 | Termin et al. | |
| 5,071,425 A | 12/1991 | Gifford, III et al. | |
| 5,085,662 A | 2/1992 | Willard | |
| 5,087,265 A | 2/1992 | Summers | |
| 5,100,423 A | 3/1992 | Fearnot | |
| 5,100,424 A | 3/1992 | Jang et al. | |
| 5,100,425 A | 3/1992 | Fischell et al. | |
| 5,102,415 A | 4/1992 | Guenther et al. | |
| 5,104,399 A | 4/1992 | Lazarus | |
| 5,108,419 A | 4/1992 | Reger et al. | |
| 5,133,733 A | 7/1992 | Rasmussen et al. | |
| 5,135,531 A | 8/1992 | Shiber | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,171,233 A | 12/1992 | Amplatz et al. | |
| 5,190,546 A | 3/1993 | Jervis | |
| 5,195,955 A | 3/1993 | Don Michael | |
| 5,215,540 A | 6/1993 | Anderhub | |
| 5,224,953 A | 7/1993 | Morgentaler | |
| 5,306,286 A | 4/1994 | Stack et al. | |
| 5,314,444 A | 5/1994 | Gianturco | |
| 5,314,472 A | 5/1994 | Fontaine | |
| 5,318,576 A | 6/1994 | Plassche, Jr. et al. | |
| 5,322,509 A | 6/1994 | Rickerd | |
| 5,329,942 A | 7/1994 | Gunther et al. | |
| 5,330,484 A | 7/1994 | Gunther | |
| 5,330,500 A | 7/1994 | Song | |
| 5,348,545 A | 9/1994 | Shani et al. | |
| 5,350,398 A | 9/1994 | Pavcnik et al. | |
| 5,354,310 A | 10/1994 | Garnic et al. | |
| 5,356,423 A | 10/1994 | Tihon et al. | |
| 5,358,493 A | 10/1994 | Schweich et al. | |
| 5,366,464 A | 11/1994 | Belknap | |
| 5,366,473 A | 11/1994 | Winston et al. | |
| 5,370,657 A | 12/1994 | Irie | |
| 5,370,683 A | 12/1994 | Fontaine | |
| 5,376,100 A | 12/1994 | Lefebvre | |
| 5,383,887 A | 1/1995 | Nadal | |
| 5,383,892 A | 1/1995 | Cardon et al. | |
| 5,383,926 A | 1/1995 | Lock et al. | |
| 5,387,235 A | 2/1995 | Chuter | |
| 5,395,349 A | 3/1995 | Quiachon et al. | |
| 5,397,345 A | 3/1995 | Lazerus | |
| 5,405,377 A | 4/1995 | Cragg | |
| 5,409,454 A | 4/1995 | Fischell et al. | |
| 5,415,630 A | 5/1995 | Gory et al. | |
| 5,419,774 A | 5/1995 | Willard et al. | |
| 5,421,832 A | 6/1995 | Lefebvre | |
| 5,423,742 A | 6/1995 | Theron | |
| 5,423,885 A | 6/1995 | Williams | |
| 5,425,765 A | 6/1995 | Tiefenbrun et al. | |
| 5,443,498 A | 8/1995 | Fontaine | |
| 5,449,372 A | 9/1995 | Schmaltz et al. | |
| 5,456,667 A | 10/1995 | Ham et al. | |
| 5,462,529 A | 10/1995 | Simpson et al. | |
| 5,476,104 A | 12/1995 | Sheahon | |
| 5,484,418 A | 1/1996 | Quiachon et al. | |
| 5,507,767 A | 4/1996 | Maeda et al. | |
| 5,512,044 A | 4/1996 | Duer | |
| 5,527,354 A | 6/1996 | Fontaine et al. | |
| 5,536,242 A | 7/1996 | Willard et al. | |
| 5,540,707 A | 7/1996 | Ressemann et al. | |
| 5,549,626 A | 8/1996 | Miller et al. | |
| 5,562,724 A | 10/1996 | Vowerk et al. | |
| 5,569,274 A | 10/1996 | Rapacki et al. | |
| 5,569,275 A | 10/1996 | Kotula et al. | |
| 5,634,897 A | 6/1997 | Dance et al. | |
| 5,658,263 A | 8/1997 | Dang et al. | |
| 5,658,296 A | 8/1997 | Bates et al. | |
| 5,662,671 A | 9/1997 | Barbut et al. | |
| 5,669,933 A | 9/1997 | Simon et al. | |
| 5,695,519 A | 12/1997 | Summers et al. | |
| 5,709,704 A | 1/1998 | Nott et al. | |
| 5,720,764 A | 2/1998 | Naderlinger | |
| 5,728,066 A | 3/1998 | Daneshvar | |
| 5,733,248 A | 3/1998 | Adams et al. | |
| 5,746,758 A | 5/1998 | Nordgren et al. | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,792,300 A | 8/1998 | Inderbitzen et al. | |
| 5,795,322 A | 8/1998 | Boudewijn | |
| 5,797,952 A | 8/1998 | Klein | |
| 5,800,413 A | 9/1998 | Swartz et al. | |
| 5,800,457 A | 9/1998 | Gelbfish | |
| 5,800,525 A | 9/1998 | Bachinski et al. | |
| 5,807,398 A | 9/1998 | Shaknovich | |
| 5,810,874 A | 9/1998 | Lefebvre | |
| 5,814,064 A | 9/1998 | Daniel et al. | |
| 5,817,102 A | 10/1998 | Johnson et al. | |
| 5,827,324 A | 10/1998 | Cassell et al. | |
| 5,833,644 A | 11/1998 | Zadno-Azizi et al. | |
| 5,833,650 A | 11/1998 | Imran | |

| | | |
|---|---|---|
| 5,846,260 A | 12/1998 | Maahs |
| 5,848,964 A | 12/1998 | Samuels |
| 5,876,367 A | 3/1999 | Kaganov et al. |
| 5,891,057 A | 4/1999 | Chaisson et al. |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky et al. |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,941,869 A | 8/1999 | Patterson et al. |
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler et al. |
| 5,976,172 A | 11/1999 | Homsma et al. |
| 5,980,555 A | 11/1999 | Barbut et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,021,340 A | 2/2000 | Randolph et al. |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,159,187 A | 12/2000 | Park et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,558,368 B1 | 5/2003 | Voda |
| 6,626,886 B1 | 9/2003 | Barbut |
| 6,740,073 B1 | 5/2004 | Saville |
| 7,621,904 B2 * | 11/2009 | McFerran et al. ........... 604/525 |
| 2001/0041881 A1 * | 11/2001 | Sarge et al. ................. 604/525 |
| 2002/0156460 A1 | 10/2002 | Ye et al. |
| 2004/0015151 A1 | 1/2004 | Chambers |

FOREIGN PATENT DOCUMENTS

| | | |
|---|---|---|
| DE | 3417738 A1 | 11/1985 |
| DE | 4030998 A1 | 10/1990 |
| EP | 0200688 A1 | 11/1986 |
| EP | 0293605 A1 | 12/1988 |
| EP | 0411118 A1 | 2/1991 |
| EP | 0427429 A2 | 5/1991 |
| EP | 0437121 B1 | 7/1991 |
| EP | 0472334 A1 | 2/1992 |
| EP | 0472368 A2 | 2/1992 |
| EP | 0533511 A1 | 3/1993 |
| EP | 0655228 A1 | 11/1994 |
| EP | 0686379 A2 | 6/1995 |
| EP | 0696447 A2 | 2/1996 |
| EP | 0737450 A1 | 10/1996 |
| EP | 0743046 A1 | 11/1996 |
| EP | 0759287 A1 | 2/1997 |
| EP | 0771549 A2 | 5/1997 |
| EP | 0784988 A1 | 7/1997 |
| EP | 0829270 A2 | 3/1998 |
| EP | 0852132 A1 | 7/1998 |
| EP | 0934729 A1 | 8/1999 |
| EP | 1123714 A2 | 8/2001 |
| EP | 1208867 A2 | 5/2002 |
| FR | 2580504 A1 | 10/1986 |
| FR | 2643250 A1 | 8/1990 |
| FR | 2666980 A1 | 3/1992 |
| FR | 2768326 A1 | 3/1999 |
| GB | 2020557 B1 | 1/1983 |
| JP | 8187294 A1 | 1/2010 |
| SU | 764684 A1 | 9/1980 |
| WO | 8809683 A1 | 12/1988 |
| WO | 9203097 A1 | 3/1992 |
| WO | 9414389 A1 | 7/1994 |
| WO | 9424946 A1 | 11/1994 |
| WO | 9601591 A1 | 1/1996 |
| WO | 9604875 A1 | 2/1996 |
| WO | 9610375 A1 | 4/1996 |
| WO | 9619941 A1 | 7/1996 |
| WO | 9623441 A1 | 8/1996 |
| WO | 9633677 A1 | 10/1996 |
| WO | 9717100 A1 | 5/1997 |
| WO | 9727808 A1 | 8/1997 |
| WO | 9742879 A1 | 11/1997 |
| WO | 9802084 A2 | 1/1998 |
| WO | 9802112 A1 | 1/1998 |
| WO | 9823322 A1 | 6/1998 |
| WO | 9833443 A1 | 8/1998 |
| WO | 9834673 A1 | 8/1998 |
| WO | 9838786 A1 | 8/1998 |
| WO | 9838920 A1 | 9/1998 |
| WO | 9838929 A1 | 9/1998 |

| | | | |
|---|---|---|---|
| WO | 9839046 A1 | 9/1998 |
| WO | 9839053 A1 | 9/1998 |
| WO | 9846297 A1 | 10/1998 |
| WO | 9847447 A1 | 10/1998 |
| WO | 9849952 A1 | 11/1998 |
| WO | 9850103 A1 | 11/1998 |
| WO | 9851237 A1 | 11/1998 |
| WO | 9855175 A1 | 12/1998 |
| WO | 9856448 A1 | 12/1998 |
| WO | 9909895 A1 | 3/1999 |
| WO | 9922673 A1 | 5/1999 |
| WO | 9923976 A1 | 5/1999 |
| WO | 9925252 A1 | 5/1999 |
| WO | 9930766 A1 | 6/1999 |
| WO | 9940964 A1 | 8/1999 |
| WO | 9942059 A2 | 8/1999 |
| WO | 9944510 A1 | 9/1999 |
| WO | 9944542 A2 | 9/1999 |
| WO | 9955236 A1 | 11/1999 |
| WO | 9958068 A2 | 11/1999 |
| WO | 0007655 A1 | 2/2000 |
| WO | 0009054 A1 | 2/2000 |
| WO | 0016705 A1 | 3/2000 |
| WO | 0049970 A1 | 8/2000 |

OTHER PUBLICATIONS

"Endovascular Grafts, Stents Drive Interventional Radiology Growth," Cardiovascular Device Update, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," AJR, 141:601-604 (Sep. 1983).

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Carotid Interventions," J. Endovasc. Surg., 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," The New England Journal of Medicine, 339 (10):659-666 (Sep. 1988).

Jordan, Jr. et al.,"Microemboli Detected by Transcranial Doppler Monitoring . . . ," Cardiovascular Surgery, 7(1) 33-38 (Jan. 1999).

Lesh, "Can Catheter Ablation Cure Atrial Fibrillation?" ACC Current Journal Review, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplast . . . ," American Heart Journal, 125(2 pt 1):362-366 (Feb. 1993).

Mazur et al.,"Directional Atherectomy with the Omnicath: A Unique New Catheter System," Catheterization and Cardiovascular Diagnosis, 31:17-18 (1994).

Moussa, MD,Issaam "Stents Don't Require Systemic Anticoagulation . . . But the Technique (and Results) Muct be Optimal," Journal of Invasive Cardiol., 8(E):3E-7E, (1996).

Nakanishi et al., "Catheter Intervention to Venous System Using Expandable Metallic Stents," Rinsho Kyobu Geka, 14 (2):English Abstract Only (Apr. 1994).

Onal et al., "Primary Stenting for Complex Atherscletoric Plaques in Aortic and Iliac Stenoses," Cardiovascular & Interventional Radiology, 21 (5):386-392 (1998).

Theron et al., "New Triple Coaxial Catheter System for Carotid Angioplasty with Cerebral Protection," American journal of Neuroradiology, 11:869-874 (1990).

Tunick et al., "Protruding atherosclerotic plaque in the aortic archo of patients with systemic embolization: A new finding seen by transesophageal echocardiography," American Heart Journal 120(3):658-660 (Sep. 1990).

Waksman et al., "Distal Embolization is Common After Directional Atherectomy . . . ," American Heart Journal, 129 (3):430-435 (1995).

Wholey, Mark H. et al., PTA and Stents in the Treatment of Extracranial Circulation, The Journal of Invasive Cardiology, 8(E): 25E-30E (1996).

Boston Scientific, "Excelsior SL-10 Microcatheters", http://www.bostonscientific.com/med_specialty/deviceDetail.jhtml?task=tskBasicDevice.j, Jul. 24, 2004, 2 pgs.

* cited by examiner

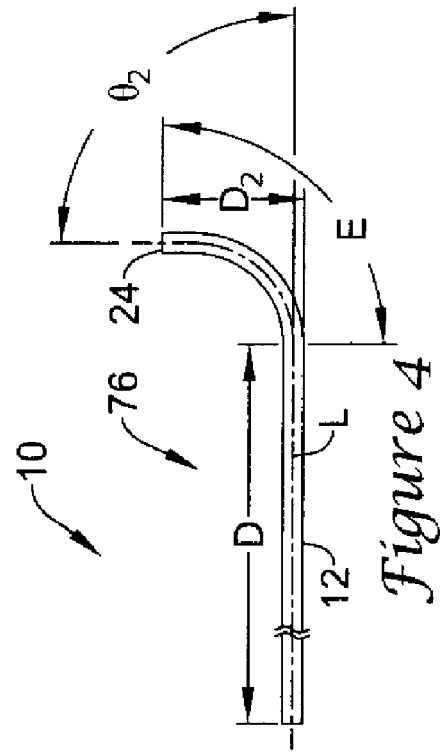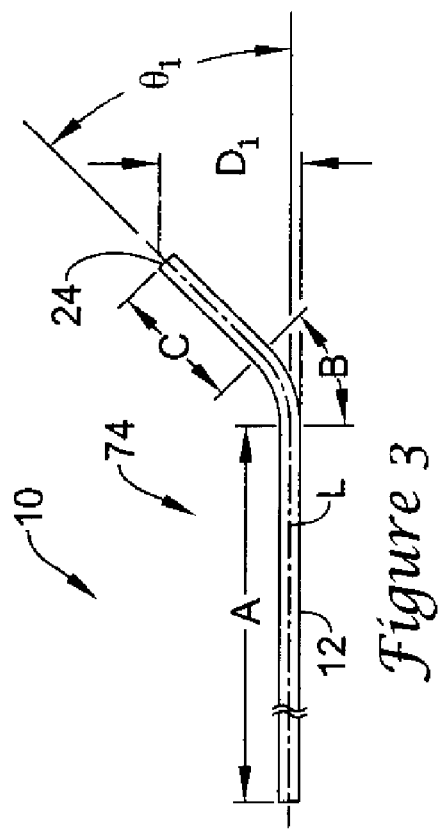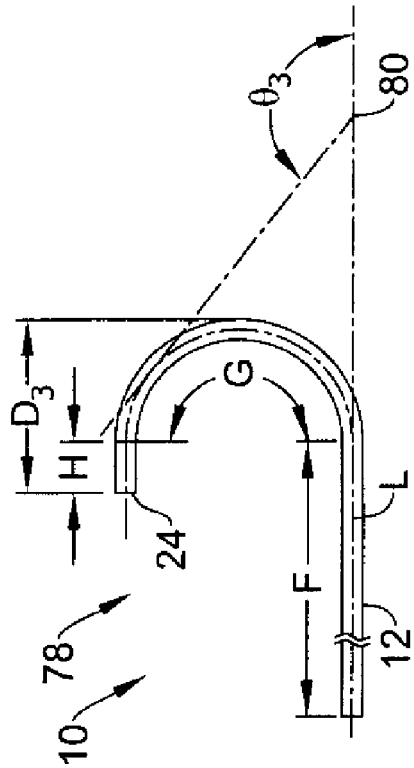
Figure 3
Figure 4
Figure 5

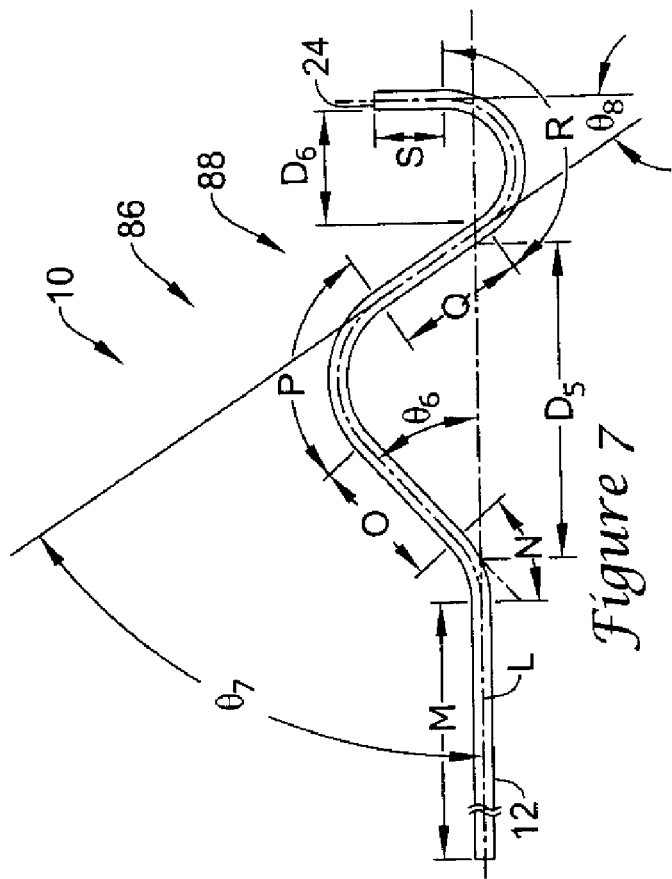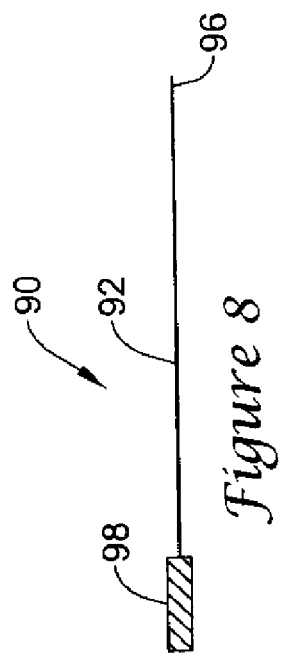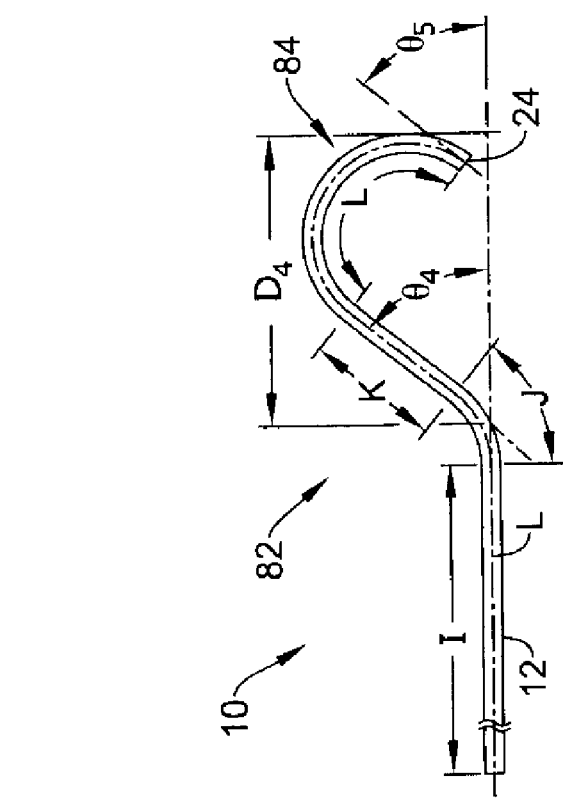

__US 7,896,861 B2__

CATHETER WITH A PRE-SHAPED DISTAL TIP

RELATED APPLICATIONS

This application is a continuation of U.S. application Ser. No. 10/970,204 filed Oct. 21, 2004, now U.S. Pat. No. 7,621,904.

FIELD

The present invention relates generally to the field of medical devices. More specifically, the present invention pertains to catheters having a pre-shaped distal tip.

BACKGROUND

Medical catheters such as guide catheters are utilized in a wide variety of interventional procedures to facilitate advancement of therapeutic devices to target locations within the body. In applications involving the neurovasculature, for example, such devices can be used in conjunction with a guidewire to advance an endovascular coil, atherectomy catheter, drug delivery catheter, or other such therapeutic device to select vascular regions within the body to treat vascular disease.

In certain applications, it may be desirable to impart a particular shape to the catheter tip to facilitate tracking of the catheter through tortuous anatomy, or to advance the catheter beyond a lesion or other obstruction within the body. In the treatment of aneurysms, for example, such shaped catheter tips can be used to reach select vascular regions within the body such as the anterior communicating artery or the posterior communicating artery. Once positioned, such tip shapes can also be used to maintain the stability of the catheter at the site of the aneurysm by using the tip shape to stabilize a portion of the catheter body against the vessel wall while maintaining the tip at the site of the aneurysm.

Shaping of catheter tips is typically accomplished in a clinical or surgical setting by bending the tip manually to a desired shape, and then setting the shape within the aid of shaping equipment. In a steam-shaping process, for example, the shape of the catheter tip is typically formed by the physician bending the tip to a particular shape and then steaming the tip to impart the desired shape. While a number of different shapes can be formed in this manner, such techniques often require the physician to perform additional steps in preparation for the procedure, thus increasing the time required to perform the interventional procedure. Moreover, the efficacy of such techniques is often dependent on the skill of the physician and the precision of the equipment employed.

SUMMARY

The present invention pertains to catheters having a pre-shaped distal tip. A catheter in accordance with an illustrative embodiment of the present invention can include an elongated tubular shaft having a proximal shaft section, an intermediate shaft section, a distal shaft section, and an interior lumen adapted to slidably receive a guidewire. Each of the proximal, intermediate, and distal shaft sections may include an outer layer of material adapted to transition the stiffness of the elongated tubular shaft along its length. In certain embodiments, for example, each of the shaft sections may comprise a material having a different durometer that transitions the stiffness of the shaft from a relatively stiff configuration along the proximal shaft section to a relatively flexible configuration along the distal shaft section. In some embodiments, the shaft may include an inner layer or coating of lubricious material adapted to reduce friction within the interior lumen. Other features relating to the performance and radiopacity characteristics of the catheter are also described herein.

The catheter can include a distal tip section having a pre-shaped tip configuration that can be used to facilitate tracking of the device through particular locations of the vasculature. In certain embodiments, for example, such pre-shaped tip configuration can be employed to facilitate insertion of the catheter at locations within the body such as the anterior communicating artery, the posterior communicating artery, the ophthalmic artery, the middle cerebral artery, and/or the superior cerebellar artery. The distal tip section can be pre-shaped into any number of desired tip configurations, including, for example, an angled tip configuration, a curved tip configuration, a J-shaped tip configuration, a C-shaped tip configuration, and an S-shaped tip configuration. In use, such pre-shaped tip configurations may reduce the shape variability that can result from shaping the catheter tip manually in a clinical or surgical setting, and may reduce the overall time required to perform the interventional procedure.

BRIEF DESCRIPTION OF THE DRAWINGS

FIG. 3 is a side plan view showing the catheter of FIG. 1 equipped with a distal tip section in accordance with an illustrative embodiment having an angled tip configuration;

FIG. 4 is a side plan view showing the catheter of FIG. 1 equipped with a distal tip section in accordance with an illustrative embodiment having a curved tip configuration;

FIG. 5 is a side plan view showing the catheter of FIG. 1 equipped with a distal tip section in accordance with an illustrative embodiment having a J-shaped tip configuration;

FIG. 6 is a side plan view showing the catheter of FIG. 1 equipped with a distal tip section in accordance with an illustrative embodiment having a C-shaped tip configuration;

FIG. 7 is a side plan view showing the catheter of FIG. 1 equipped with a distal tip section in accordance with an illustrative embodiment having an S-shaped tip configuration; and FIG. 8 is a side plan view of an illustrative shape retention mandrel for use with a catheter of the present invention.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
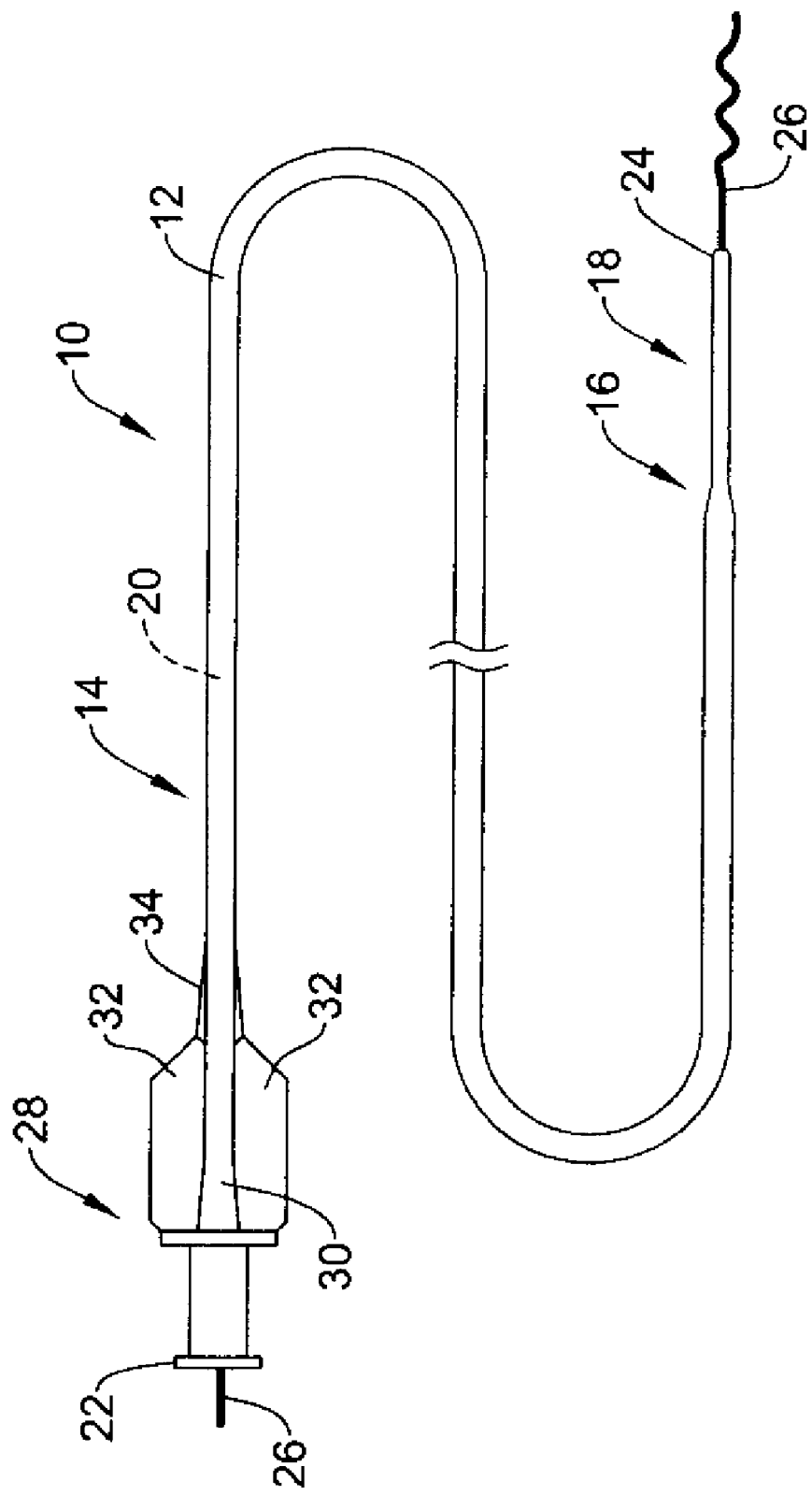
FIG. 1 is a plan view showing a catheter in accordance with an exemplary embodiment of the present invention.

FIG. 1 is a plan view of a catheter 10 in accordance with an exemplary embodiment of the present invention. Catheter 10, illustratively a guide catheter for use in neurovascular and peripheral interventions, includes an elongated tubular shaft 12 having a proximal shaft section 14, an intermediate shaft section 16, and a distal shaft section 18. The shaft 12 may define an interior lumen 20, which in the illustrative embodiment of FIG. 1 extends from a proximal end 22 of the catheter 10 to a distal end 24 thereof. In certain embodiments, the interior lumen 20 of the shaft 12 can be configured to slidably receive a guidewire 26 that can be used to track other therapeutic devices to target locations within the body. In certain applications, for example, catheter 10 can be used to facilitate advancement of the guidewire 26 to select vascular regions within the body such as the anterior communicating artery or posterior communicating artery for the treatment of aneurysms.

The proximal shaft section 14 can include a hub and strain relief assembly 28 that can be used as an aid to manipulate the catheter 10 from a location outside of the body. The hub and strain relief assembly 28 may include a main body 30 having a number of fins 32 that can be used to improve gripping and to facilitate labeling for product identification, and a strain relief member 34 adapted to provide additional column strength and rigidity to the proximal shaft section 14. A second strain relief member (not shown) may be disposed on the shaft 12 distally of strain relief member 34 to provide additional strain relief to the proximal shaft section 14 of the catheter 10, if desired.

The length of the various shaft sections 14, 16, 18 may vary depending on the particular location within the body to be traversed, and the performance characteristics (e.g. flexibility, column strength, etc.) desired in the catheter 10. In certain embodiments, for example, the proximal shaft section 14 may be made available in 80 cm, 105 cm, and 125 cm embodiments, although other lengths are possible. In such embodiments, the overall length of the catheter 10 may be 105 cm, 130 cm, and 150 cm, respectively, which is typical for catheters employed in neurovascular and/or peripheral interventions. It should be understood, however, that the length of the catheter 10 may vary to permit the catheter 10 to be used at other locations within the body and/or to perform other types of interventional procedures.

Figure 2:
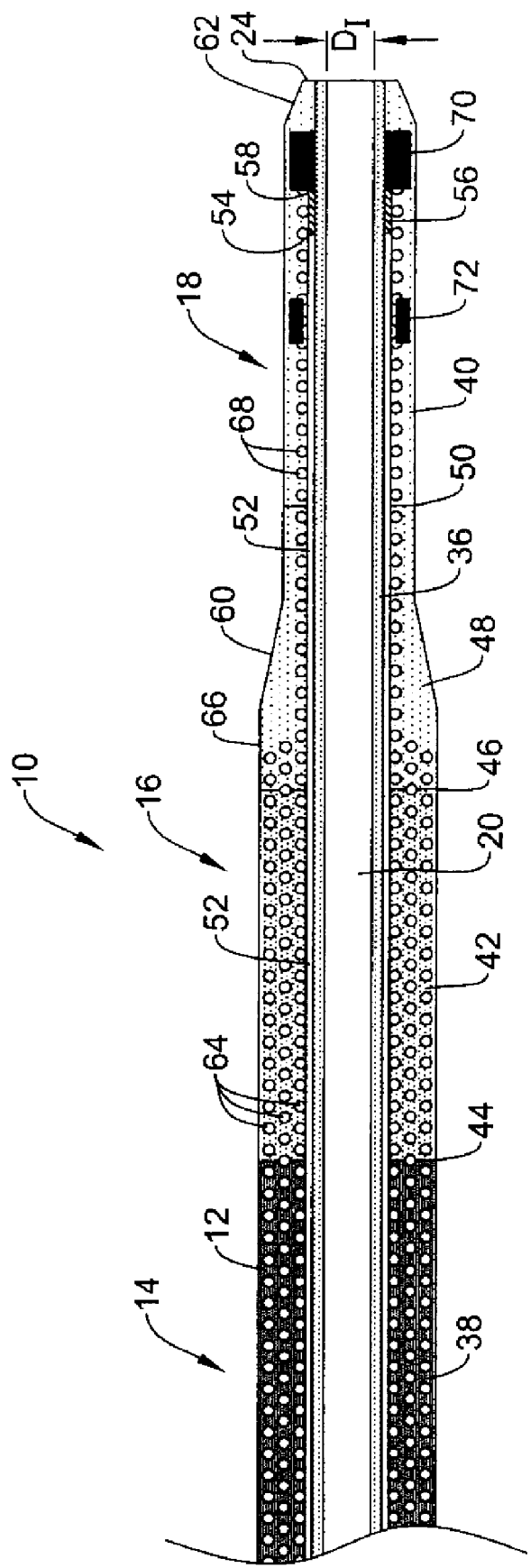
FIG. 2 is a longitudinal cross-sectional view showing a distal portion of the catheter of FIG. 1 in greater detail.

FIG. 2 is a longitudinal cross-sectional view showing a distal portion of the catheter 10 of FIG. 1 in greater detail. As can be seen in FIG. 2, the shaft 12 can include an inner layer or coating 36 of lubricious material that extends along all or a portion of the catheter 10. In certain embodiments, for example, the inner layer or coating 36 may comprise a hydrophilic polymer material that reduces friction within the interior lumen 20. An example of such lubricious material is polytetrafluoroethylene (PTFE), which is commercially available from Dupont under the trademark TEFLON®. Other materials such as polyethylene (PE), polypropylene (PP), polyvinylchloride (PVC), ethylvinylacetate (EVA), polyurethanes, polyamides, polyethyleneteraphthalate (PET), ethylene-chlorofluoroethylene (ECTFE), fluorinated ethylenepropylene (FEP), polychlorotrifluoroethylene (PCTFE), polyvinylfluoride (PVF), polyvinylidenefluoride (PVDF), and their mixtures and/or copolymers thereof may also be employed, if desired.

The interior lumen 20 may be uniform along the proximal, intermediate, and distal shaft sections 14, 16, 18 of the catheter 10, or may vary in dimension at one or more locations along the length of the shaft 12, if desired. In the illustrative embodiment depicted in FIG. 2, for example, the interior lumen 20 is substantially uniform along the entire length of the shaft 12, having an inner diameter $D_1$ in the range of about 0.012 to 0.021 inches, and more specifically 0.014 to 0.019 inches, which is sufficiently large to permit many conventional guidewires to be inserted and advanced through the interior lumen 20. The inner diameter $D_1$ may be made larger or smaller, however, to permit other sized guidewires and/or other intravascular devices to be advanced through the interior lumen 20, if desired.

The shaft 12 may further a number of outer layers that can be used to transition the stiffness of the shaft 12 from a relatively stiff configuration along the proximal shaft section 14 to a relatively flexible configuration along the distal shaft section 18. In certain embodiments, for example, each of the proximal, intermediate, and distal shaft sections 14, 16, 18 may comprise a different polymeric material adapted to impart a desired strength, flexibility, hardness, and/or other desired characteristic to the catheter 10. In the illustrative embodiment of FIG. 2, for example, proximal shaft section 14 may include an outer layer segment 38 of material having a relatively high durometer whereas the distal shaft section 18 may include an outer layer segment 40 of material having a relatively low durometer. In one such embodiment, the outer layer segment 38 of the proximal shaft section 14 may comprise a relatively stiff polymeric material such as PEBAX® 7233 whereas the outer layer segment 40 of the distal shaft section 18 may comprise relatively flexible polymeric material such as PEBAX® 2533. The outer layer segments 38, 40 may each comprise a single polymer, multiple polymers, or a blend of polymers, as desired.

To further transition the stiffness along the length of the shaft 12, the intermediate shaft section 16 can include one or more outer layer segments comprising a material having a durometer that is intermediate to that of the proximal and distal shaft sections 14, 18. In one illustrative embodiment, for example, the intermediate shaft section 16 may include a first outer layer segment 42 of PEBAX® 5533 that spans the length of the shaft 12 from a first location 44 to a second location 46 thereof. A second outer layer segment 48 of PEBAX® 4033 can be provided along the portion of the intermediate shaft section 16 extending from the second location 46 to a third location 50 thereof. While the illustrative embodiment of FIG. 2 shows the use of two outer layer segments 42, 48 along the length of the intermediate shaft section 16, it should be understood that a greater or lesser number of segments can be provided, if desired. Moreover, as with the outer layer segments 38, 40 of the proximal and distal shaft sections 14, 18, the outer layer segments 42, 48 of the intermediate shaft section 16 can include a single polymer, multiple polymers, or a blend of polymers, as desired.

In certain embodiments, an intermediate layer of material can be provided between the inner layer 36 and the various outer layers segments 38, 40, 42, 48 of the shaft 12 to further transition the stiffness of the catheter 10. As shown in FIG. 2, for example, a first intermediate layer segment 52 can be provided about the inner layer 36 along a portion of the proximal, intermediate, and distal shaft sections 14, 16, 18, terminating distally at a location 54 proximal to the distal end 24 of the shaft 12. The first intermediate layer segment 52 may comprise a polymeric material such as PEBAX® 5533 having an elasticity sufficient to permit the distal portion of the catheter 10 to radially flex or bend while providing additional column strength to withstand buckling or kinking as the catheter 10 is tracked through the body. The first intermediate layer segment 52 may further act as a tie layer in certain embodiments to facilitate bonding of the inner layer 36 with the various outer layer segments 38, 40, 42, 48 of the shaft 12.

In some embodiments, a second intermediate layer segment 56 may be provided about the inner layer 36 along a portion of the distal shaft section 18, extending from location 54 to a second location 58 proximal to the distal end 24 of the catheter 10. In contrast to intermediate layer segment 52 described above, the second intermediate layer segment 56 may comprise a relatively flexible material such as PEBAX® 2533, which further aids in transitioning the stiffness along the length of the distal shaft section 18.

The wall thickness of the various shaft sections 14, 16, 18 may be reduced along one or more sections of the shaft 12 to transition the flexibility, torqueability, and other desired characteristics of the catheter 10. In certain embodiments, for example, the proximal shaft section 14 may have a wall thickness in the range of about 0.01 to 0.02 inches, and more specifically 0.015 inches, whereas the distal shaft section 18 may have a smaller wall thickness in the range of about 0.004 to 0.006 inches, and more specifically 0.0055 inches. To further transition the stiffness, the intermediate shaft section 16 may include a tapered section 60 wherein the profile of the catheter 10 transitions from about 2.4 Fr. to about 1.7 Fr. If desired, a second tapered section 62 can be provided along the distal shaft section 18 to further reduce the profile at the distal end 24 of the catheter 10.

A reinforcement member (e.g. a braid, weave, etc.) can be provided along all or a portion of the shaft length, providing additional stiffness and torsional rigidity to the catheter 10, if desired. The reinforcement member may include a first coil segment comprising three wire coil layers 64 disposed along the length of the shaft 12 from a location at or near the strain relief member 34 to a location 66 along the intermediate shaft section 16. As shown in FIG. 2, the coil layers 64 forming the first coil segment can be encased entirely within the outer layers 38, 42, 48 of the proximal and intermediate shaft section 14,16.

A second coil segment comprising a single wire coil layer 68 may extend distally from location 66 along the intermediate shaft section 16 to a point at or near location 58 along the distal shaft section 18. In contrast to the first coil segment, the second coil segment may have a greater amount of flexibility to facilitate bending or flexion of the distal portion of the catheter 10 as it is advanced through tortuous anatomy. As with the wire coil layers 64 forming the first coil segment, the single wire coil layer 68 can be encased entirely within the outer layers 40,48 of the intermediate and distal shaft sections 16,18.

While two coil segments are specifically depicted in the embodiment of FIG. 2, it should be understood that a greater or lesser number of coil segments can be provided, either continuously or at discrete intervals along the length of the shaft 12. Moreover, while the transition in stiffness along the length of the shaft 12 can be accomplished by varying the number of coil layers encased within the shaft 12, other factors such as the size of the coils employed, the material selection, and/or the pitch of the coils can also be varied to alter the performance characteristics of the catheter 10. In the latter case, for example, the coil pitch of the coils 68 forming the second coil segment can be made greater than the coil pitch of the coils 64 forming the first coil segment, thus imparting a greater amount of flexibility to the distal portion of the catheter 10. The types of wire or wires (e.g. round, flat, etc.) used in forming the various coil segments may also be altered to change the performance characteristics of the catheter 10, if desired. In certain embodiments, the selection of materials used to form each of the coil segments can also be varied to impart a desired flexibility to the catheter 10.

The catheter 10 may include one or more radiopaque features that permit the device to be visualized within the body using a fluoroscope or other such device. In certain embodiments, for example, a distal radiopaque marker 70 encased within the distal shaft section 18 can be provided to permit the physician to radiographically visualize the distal end 24 of the catheter 10 as it is advanced through the body. The distal radiopaque marker 70 may include a suitable material such as platinum, gold, or tantalum, or a combination of materials such as platinum/iridium that can be used to radiographically determine the location of the catheter 10 within the vasculature. The distal radiopaque marker 70 should typically be placed at or near the distal end 24 of the shaft 12 to permit the physician to accurately determine the location of the catheter tip. In some embodiments, for example, the radiopaque marker can be positioned at a location about 0.75 cm away from the distal end 24 of the catheter 10. It should be understood, however, that other placement positions are possible.

In certain embodiments, the catheter 10 may further include a proximal radiopaque marker 72 encased with the distal shaft section 18 at a location proximal to the distal radiopaque marker 70. In the treatment of brain aneurisms, for example, such proximal radiopaque marker 72 can be used to align the coil delivery wire used in many endovascular coiling procedures. As with the distal radiopaque marker 70, the proximal radiopaque marker 72 can include a radiopaque material or combination of radiopaque materials that provide sufficient contrast to permit fluoroscopic visualization. The placement location of the proximal radiopaque marker 72 will typically vary based on the particular anatomy to be traversed, and the type of intravascular device to be inserted through the interior lumen 20. In endovascular coiling techniques involving the neurovasculature, for example, the proximal radiopaque marker band 72 can be placed at a location of about 30 cm from the distal end 24 of the shaft 12, although other placement positions are possible.

To further aid in visualization of the catheter 10 within the body, one or more of the shaft sections 14, 16, 18 can be loaded or otherwise include a radiopaque material. In certain embodiments, for example, the proximal, intermediate, and distal shaft sections 14, 16, 18 may be loaded with tungsten (W), bismuth subcarbonate ($(BiO_2)CO_3$), barium sulfate ($BaSO_4$) or other suitable radiopaque agent. The amount of loading may vary depending on the amount of radiopacity necessary to provide sufficient visibility of the catheter 10 on a fluoroscopic monitor. In embodiments employing a radiopaque filler of $BaSO_4$, for example, a 20% by weight concentration will typically provide sufficient visibility of the catheter 10 within the body. It should be understood, however, that other factors such as the wall thickness and material composition of the shaft 12 can also affect the amount of loading necessary to provide sufficient visibility.

In some embodiments, all or a portion of the outer surface of the catheter 10 may include a lubricious coating that can be used to facilitate tracking of the catheter 10 through the tortuous anatomy and/or beyond lesions or other obstructions within the body. Examples of suitable lubricous materials may include hydrophilic polymers such as polyarylene oxides, polyvinylpyrolidones, polyvinylalcohols, hydroxy alkyl cellulsics, aligns, saccharides, caprolactones, and the like, or mixtures and combinations thereof. Lubricious materials such as that described above with respect to the inner layer or coating 36 can also be utilized, if desired.

The coated length along which the lubricious coating is applied to the catheter 10 may vary depending on the overall length of the shaft 12. In those embodiments where the overall length of the catheter 10 is approximately 150 cm, for example, the length of the lubricious coating may be provided on the distal-most 100 cm length of the shaft 12, providing additional lubricity to the leading portion of the catheter 10. Conversely, in those embodiments where the overall length of the catheter is approximately 130 cm and 105 cm, the length of the lubricious coating may be provided on a 97 cm and 72 cm length of the shaft 12, respectively, providing additional lubricity in those embodiments. The length and/or placement location of the lubricious coating may vary, however, depending on the performance characteristics desired in the catheter 10 as well as other factors.

The catheter 10 can include a number of pre-shaped tip configurations that can be used to facilitate tracking of the device through select locations within the vasculature. In some cases, such pre-shaped tip configurations may reduce the shape variability that often results from shaping the tip manually in a clinical or surgical setting. Moreover, such pre-formed tip shapes may reduce the overall time required to perform the interventional procedure by obviating the need to shape the tip just prior to insertion within the patient's body.

FIG. 3 is a side plan view showing the catheter 10 of FIG. 1 equipped with a distal tip section 74 in accordance with an illustrative embodiment of the present invention having an angled tip configuration. As can be seen in FIG. 3, the distal tip section 74 of catheter 10 may include a first straight section A of the shaft 12, a curved section B of the shaft 12 extending distally of the first straight section A, and a second straight section C of the shaft 12 extending distally from the curved section B.

The curved section B of the shaft 12 can be configured to orient the distal end 24 at an angle $\theta_1$ relative to a general longitudinal axis L of the shaft 12. In certain embodiments, for example, the curved section B can be configured to orient the second straight section C at an angle $\theta_1$ of about 25° to 65°, and more specifically 35° to 55° relative to the longitudinal axis L. Angles $\theta_1$ greater or lesser than these ranges can be employed, however.

The distal end 24 of the catheter 10 can be located a distance $D_1$ away from the outer periphery of the first straight section A, which, in certain embodiments, may represent the maximum profile of the distal tip section 74. The angle $\theta_1$ at which the second straight section C is oriented relative to the longitudinal axis L as well as the length of the second straight section C can be varied to permit the catheter 10 to be used in particular locations of the patient's anatomy. In neurological and peripheral interventions, for example, such dimensions can be selected to form a distal tip section 74 having a profile (i.e. $D_1$ dimension) of approximately 0.22 inches, allowing the catheter 10 to be easily inserted into difficult anatomy such as the anterior or posterior communicating artery.

FIG. 4 is a side plan view showing the catheter 10 of FIG. 1 equipped with a distal tip section 76 in accordance with an illustrative embodiment of the present invention having a curved tip configuration. As can be seen in FIG. 4, the distal tip section 76 of catheter 10 may include a straight section D of the shaft 12, and a curved section F of the shaft 12 extending distally from the straight section D.

The curved section E of the shaft 12 can be configured to orient the distal end 24 at an angle $\theta_2$ relative to the general longitudinal axis L of the catheter 10. In the illustrative embodiment depicted in FIG. 4, for example, the distal end 24 of the catheter 10 is shown oriented at angle $\theta_2$ of approximately 90°. It should be understood, however, that the curved section E of the shaft 12 can be configured to orient the distal end 24 at an angle $\theta_2$ greater or lesser than 90°, if desired.

As with the embodiment of FIG. 3, the distal end 24 of the catheter 10 can be located a distance $D_2$ away from the outer periphery of the straight section D, which, in certain embodiments, may represent the maximum profile of the distal tip section 76. In one illustrative embodiment, for example, the curved section E of the shaft 12 can be configured such that the distal end 24 is located a distance $D_2$ of approximately 0.22 inches away from the outer periphery of the straight section D. Other configurations are, of course, possible.

FIG. 5 is a side plan view showing the catheter 10 of FIG. 1 equipped with a distal tip section 78 in accordance with an illustrative embodiment of the present invention having a J-shaped tip configuration. As can be seen in FIG. 5, the distal tip section 78 of catheter 10 may include a first straight section F of the shaft 12, a curved section G of the shaft 12 extending distally from the first straight section F, and a second straight section H of the shaft 12 extending distally from the curved section G.

In the illustrative embodiment of FIG. 5, the curved section G of the shaft 12 can be configured to orient the distal end 24 in a proximal direction, forming a J-shaped portion of the catheter 10. The rise and run of the curved section G may be defined generally by reference to angle $\theta_3$, which defines the angle at which a tangent line intersects the curved section G from a known point 80 along the longitudinal axis L. In certain embodiments, for example, the curved section G may define an angle $\theta_3$ of approximately 170°, orienting the distal end 24 of the shaft 12 proximally a distance $D_3$ (e.g. 0.2 inches) away from the distal-most portion of the curved section G.

FIG. 6 is a side plan view showing the catheter 10 of FIG. 1 equipped with a distal tip section 82 in accordance with an illustrative embodiment of the present invention having a C-shaped tip configuration. As can be seen in FIG. 6, the distal tip section 82 of catheter 10 may include a first straight section I of the shaft 12, a first curved section J of the shaft 12 extending distally from the first straight section I, a second straight section K of the shaft 12 extending distally from the first curved section J, and a second curved section L of the shaft 12 extending distally from the second straight section K.

The first curved section J of the shaft 12 can be configured to orient the second straight section K at an angle $\theta_4$ relative to the general longitudinal axis L of the catheter 10. The second curved section L of the shaft 12, in turn, can be configured to orient the distal end 24 at an angle $\theta_5$ relative to the general longitudinal axis L. The various angles $\theta_4$, $\theta_5$ and section lengths can be selected to form a C-shaped section 84 having an overall length defined by dimension $D_4$, which in the illustrative embodiment of FIG. 6 extends from the distal end of the first straight section I to the distal-most portion of the second curved section L. The particular length $D_4$ imparted to the distal tip section 82 may vary depending on the intended use of the catheter 10. In neurological and peripheral interventions, for example, the C-shaped section 84 can be configured to have a length $D_4$ of about 0.5 inches, although other lengths are possible.

FIG. 7 is a side plan view showing the catheter 10 of FIG. 1 equipped with a distal tip section 86 in accordance with an illustrative embodiment of the present invention having an S-shaped tip configuration. As can be seen in FIG. 7, the distal tip section 86 of catheter 10 may include a first straight section M of the shaft 12, a first curved section N of the shaft 12 extending distally from the first straight section M, a second straight section O of the shaft 12 extending distally from the first curved section N, a second curved section P of the shaft 12 extending distally from the second straight section O, a third straight section Q of the shaft 12 extending distally from the second curved section P, a third curved section R of the shaft 12 extending distally from the third straight section Q, and a fourth straight section S of the shaft 12 extending distally from the third curved section R.

The first curved section N of the shaft 12 can be configured to orient the second straight section O at an angle $\theta_6$ away from the general longitudinal axis L of the shaft 12. The second curved section P of the shaft 12, in turn, can be configured to orient the third straight section Q at an angle $\theta_7$ relative to the longitudinal axis L. The distance $D_5$ between the distal end of the first straight section M and the portion of the third straight section Q crossing the longitudinal axis L may define the first leg of an S-shaped portion 88 of the distal tip section 86.

As can be further seen in FIG. 7, the third curved section R may bend and orient the fourth straight section S of the shaft 12 at an angle $\theta_8$ relative to the third straight section Q, forming a second leg of the S-shaped section 88 having a length defined by distance $D_6$. The various section lengths and angles can also be selected such that length $D_6$ of the second leg is smaller than the length $D_5$ of the first leg. In one illustrative embodiment, for example, the length $D_6$ of the second leg can be approximately 0.08 inches whereas the length $D_5$ of the first leg can be approximately 0.36 inches. Other configurations wherein the length $D_6$ of the second leg is greater than or substantially equal to the length $D_5$ of the first leg can also be employed, if desired. In some embodiments, the overall length (i.e. $D_5+D_6$) of the S-shaped section 88 can be approximately 0.44 inches.

To retain the shape of any of the above distal tip sections 74, 76, 78, 84, 86 prior to use and/or during sterilization, a shape retention mandrel can be inserted into the interior lumen 20 of the catheter 10. As shown in FIG. 8, for example, a shape retention mandrel 90 comprising a wire member 92 having a proximal end 94 and a distal end 96 can be sized to fit within the interior lumen 20 of the catheter 10 prior to shaping. In some embodiments, a handle grip 98 coupled to the proximal end 94 of the wire mandrel 90 can be provided to facilitate insertion of the wire mandrel 90 into the catheter 10, if desired. The shape retention mandrel 90 can be provided as part of a kit or packaging containing the sterilized catheter 10, or as a separate member that is later inserted into the catheter 10 by the physician.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. A catheter, comprising:
an elongated tubular shaft having a proximal end, a proximal shaft section, an intermediate shaft section, a distal shaft section, a distal end, a length extending from the proximal end to the distal end, and an interior lumen adapted to slidably receive a guidewire, each of said proximal, intermediate, and distal shaft sections including an outer layer of material having a different durometer adapted to transition the stiffness of the elongated tubular shaft from a relatively stiff configuration along the proximal shaft section to a relatively flexible configuration along the distal shaft section;
wherein the interior lumen of the elongated tubular shaft includes an inner layer or coating of lubricious material;
wherein the proximal shaft section extends for at least about 76% of the length of the elongated tubular shaft;
an intermediate layer disposed between the elongated tubular shaft and the inner layer or coating, the intermediate layer comprising:
a first intermediate layer segment disposed about the inner layer along a portion of the proximal, intermediate, and distal shaft sections; and
a second intermediate layer segment disposed about the inner layer along a portion of the distal shaft section, the second intermediate layer segment extending distally from the first intermediate layer segment to a location proximal to the distal end of the elongated tubular shaft;
wherein the second intermediate layer segment is more flexible than the first intermediate layer segment;
a reinforcement comprising a first coil segment having a plurality of wire coil layers encased within the outer layers of the proximal and intermediate sections and a second coil segment extending distally from the first coil segment, the second coil segment comprising a single wire coil layer encased within the outer layers of the intermediate and distal sections;
wherein the first coil segment extends proximally to a strain relief member at the proximal end of the elongate tubular shaft;
wherein the first and second coil segments each have a coil pitch, wherein the coil pitch of the second coil segment is greater than the coil pitch of the first coil segment; and
a distal tip section having a pre-shaped curved tip configuration.

2. The catheter of claim 1, wherein the inner layer or coating of lubricious material includes a hydrophilic polymer.

3. The catheter of claim 1, wherein the outer layer of material forming the proximal shaft section has a durometer greater than the outer layer of material forming the distal shaft section.

4. The catheter of claim 1, wherein the outer layer of material forming the intermediate shaft section has a durometer greater than the outer layer of material forming the distal shaft section and a durometer less than the outer layer of material forming the proximal shaft section.

5. The catheter of claim 4, wherein the outer layer of the intermediate shaft section comprises a first outer layer segment formed of a first material, and a second outer layer segment formed of a second material different than the first material.

6. The catheter of claim 5, wherein the first material of said first outer layer segment has a durometer greater than the second material of said second outer layer segment.

7. The catheter of claim 1, further comprising an outer coating of lubricious material disposed about all or a portion of the elongated tubular shaft.

8. The catheter of claim 1, further comprising a first radiopaque marker encased within the distal shaft section of the elongated tubular shaft.

9. The catheter of claim 8, further comprising a second radiopaque marker encased within the distal shaft section of the elongated tubular shaft proximal to the first radiopaque marker.

10. The catheter of claim 1, wherein the elongated tubular shaft includes radiopaque filler.

11. The catheter of claim 1, wherein said pre-shaped tip configuration comprises an angled tip configuration.

12. The catheter of claim 1, wherein said pre-shaped tip configuration comprises a multi-curved tip configuration.

13. The catheter of claim 1, wherein said pre-shaped tip configuration comprises a J-shaped tip configuration.

14. The catheter of claim 1, wherein said pre-shaped tip configuration comprises a C-shaped tip configuration.

15. The catheter of claim 1, wherein said pre-shaped tip configuration comprises an S-shaped tip configuration.

16. The catheter of claim 1, further comprising a mandrel disposed within the interior lumen of the elongated tubular shaft.

* * * * *